(12) United States Patent
Manke et al.

(10) Patent No.: US 9,078,975 B2
(45) Date of Patent: Jul. 14, 2015

(54) SYRINGE HAVING PIVOTING ARM PLUNGER ROD

(71) Applicant: Becton Dickinson France, S.A.S., Le Pont-de-Claix (FR)

(72) Inventors: Darrin Scott Manke, North Andover, MA (US); Christopher Labak, Brookline, NH (US); Joseph Omer St. Cyr, Salem, NH (US)

(73) Assignee: Becton Dickinson France, S.A.S., Le Pont-de-Claix (FR)

( * ) Notice: Subject to any disclaimer, the term of this patent is extended or adjusted under 35 U.S.C. 154(b) by 188 days.

(21) Appl. No.: 13/622,383

(22) Filed: Sep. 19, 2012

(65) Prior Publication Data

US 2013/0085455 A1 Apr. 4, 2013

Related U.S. Application Data

(60) Provisional application No. 61/541,661, filed on Sep. 30, 2011.

(51) Int. Cl.
*A61M 5/315* (2006.01)

(52) U.S. Cl.
CPC ....... *A61M 5/31511* (2013.01); *A61M 5/31515* (2013.01); *A61M 2005/31518* (2013.01)

(58) Field of Classification Search
CPC ............. A61M 5/31511; A61M 5/31515; A61M 2005/31518
USPC .................. 604/110, 187, 218, 223, 227, 233
See application file for complete search history.

(56) References Cited

U.S. PATENT DOCUMENTS

| | | | |
|---|---|---|---|
| 4,011,868 A | 3/1977 | Friend | |
| 4,581,023 A | 4/1986 | Kuntz | |
| 4,639,248 A * | 1/1987 | Schweblin | 604/187 |
| 8,172,813 B2 * | 5/2012 | Janish | 604/228 |
| 2011/0046560 A1 | 2/2011 | Schiller et al. | |
| 2011/0046569 A1 | 2/2011 | Lum et al. | |
| 2011/0046603 A1 | 2/2011 | Felsovalyi et al. | |

FOREIGN PATENT DOCUMENTS

| | | |
|---|---|---|
| DE | 188449 C | 10/1906 |
| WO | 2010034462 A1 | 4/2010 |
| WO | 2012056265 A1 | 5/2012 |

\* cited by examiner

*Primary Examiner* — Nicholas Lucchesi
*Assistant Examiner* — Justin L Zamory
(74) *Attorney, Agent, or Firm* — The Webb Law Firm (57) ABSTRACT

A syringe assembly includes a syringe barrel having a first end, a second end, and a sidewall extending between the first end and the second end. The syringe assembly further includes a stopper disposed within a chamber of the syringe barrel, a plunger adapter engaged with the stopper, and a plunger rod having first and second ends. The first end of the plunger rod is pivotally secured to the plunger adapter. The plunger rod has a pre-use position where the second end of the plunger rod is positioned adjacent to the syringe barrel, and a use position where the plunger rod is configured to displace the stopper relative to the syringe barrel. A recessed portion of the plunger adapter receives a portion of the first end of the plunger rod when the plunger rod is in the pre-use position and the use position.

26 Claims, 11 Drawing Sheets

SYRINGE HAVING PIVOTING ARM PLUNGER ROD

CROSS-REFERENCE TO RELATED APPLICATION

This application claims priority to U.S. Provisional Patent Application Ser. No. 61/541,661 filed Sep. 30, 2011, the entire disclosure of which is hereby incorporated by reference.

BACKGROUND OF THE INVENTION

1. Field of the Invention

The present invention relates to a syringe adapted for delivery of a fluid and/or collection of a fluid, and, more particularly, to a syringe having a pivoting arm plunger rod.

2. Description of Related Art

Syringe assemblies, and in particular hypodermic syringes, are well known in the medical field for dispensing fluids, such as medication. A conventional syringe typically includes a syringe barrel with an opening at one end and a plunger mechanism disposed through the other end. The plunger typically includes a plunger rod extending through the barrel, with a plunger head or stopper at the end of the plunger rod within the barrel and with a finger flange at the other end of the plunger rod extending out of the barrel. In use, the plunger rod is retracted through the syringe barrel to fill the syringe barrel with a fluid, such as a medication, with the plunger rod extending out from the rear end of the syringe barrel. For delivery of the medication to a patient, the opening of the syringe barrel is adapted for fluid communication with a patient, such as through a hypodermic needle fitted at the front end of the syringe barrel or through a luer-type fitting extending from the front end of the syringe barrel for attachment with a fluid line of a patient. Upon depression of the plunger rod, the plunger rod and stopper travel through the syringe barrel, thereby forcing the contents of the syringe out through the opening at the front end for delivery to the patient. Such an operation is well known in the medical field, and medical practitioners have become well accustomed to the use of such common fluid delivery procedures through standard syringes.

Conventional syringes are well known to be used in connection with a vial of a medication, where the user draws the fluid into the syringe immediately prior to injection and delivery of the fluid to the patient. Oftentimes, hypodermic syringes may be packaged as "pre-filled" devices, wherein the syringe is pre-filled with medication prior to being packaged and delivered to the end user. In this manner, there is no need for the user to fill the device prior to injection, thereby saving time for the end user and maintaining consistent volumes for delivery.

Pre-filled syringes and pre-filled metered dose syringes are often filled with narcotics or other drugs at a production facility, packaged, and then shipped to a medical facility. Once at the facility, these syringes are often placed in controlled storage and/or locked cabinets to reduce theft of the syringes themselves and/or theft of the contents of these syringes. The space within these controlled storage locations is often limited, thus there is a need for a syringe assembly that has a smaller packaging footprint to reduce the storage space required for containing this syringe. It is also desirable to produce syringes that are uniform in terms of an outer surface shape to allow for stacking of the syringes within the storage cabinet.

SUMMARY OF THE INVENTION

In one embodiment, a syringe assembly includes a syringe barrel having a first end, a second end, and a sidewall extending between the first end and the second end. The syringe assembly further includes a stopper disposed within a chamber of the syringe barrel, a plunger adapter engaged with the stopper, and a plunger rod having first and second ends. The first end of the plunger rod is pivotally secured to the plunger adapter. The plunger rod has a pre-use position where the second end of the plunger rod is positioned adjacent to the syringe barrel and a use position where the plunger rod is configured to displace the stopper relative to the syringe barrel. A recessed portion of the plunger adapter receives a portion of the first end of the plunger rod when the plunger rod is in the pre-use position and the use position.

The stopper and the plunger adapter may be co-formed. The plunger rod may be substantially parallel to a longitudinal axis extending in a longitudinal direction through the chamber of the syringe barrel when the plunger rod is in the pre-use position and the plunger rod may be substantially aligned along the longitudinal axis of the syringe barrel when the plunger rod is in the use position. The second end of the plunger rod may engage and receive a portion of the syringe barrel when the plunger rod is in the pre-use position. The plunger rod may include an elongate body with the first end of the plunger rod including one of a receiver and an engagement pivotally secured to the other of the receiver and the engagement positioned within the recessed portion of the plunger adapter. The first end of the plunger rod may include an extension extending from the elongate body of the plunger rod.

The receiver may be positioned on the extension of the first end of the plunger rod and the engagement may be positioned within the recessed portion of the plunger adapter. The receiver may be an opening corresponding to the extension of the first end of the plunger rod, and the engagement may be a pin-shaped member configured to be received by the receiver of the plunger rod. At least a portion of the elongate body of the plunger rod may be generally T-shaped in cross-section with the recessed portion of the plunger adapter configured to receive the extension of the plunger rod and a portion of the elongate body of the plunger rod. The recessed portion of the plunger adapter may be generally cross-shaped having a first area configured to receive the extension of the plunger rod and a second area configured to receive the T-shaped cross-section of the elongate body of the plunger rod. The first end of the plunger rod may be pivotally secured to the plunger adapter at a position spaced radially inward from an external surface of the plunger adapter.

In another embodiment, a syringe assembly includes a syringe barrel having a first end, a second end, and a sidewall extending between the first end and the second end with the sidewall defining a chamber. The syringe assembly further includes a stopper, a plunger adapter engaged with the stopper, and a plunger rod having a first end pivotally secured to the plunger adapter and a second end including a thumb press having a recessed portion configured to conform to an external surface of the syringe barrel. At least a portion of the stopper is positioned within the chamber of the syringe barrel. The plunger rod has a pre-use position where the second end of the plunger rod is positioned adjacent to the syringe barrel and a use position where the second end of the plunger rod is spaced from the syringe barrel along a longitudinal axis of the syringe barrel.

The stopper and the plunger adapter may be co-formed. The syringe assembly may further include a luer lock positioned adjacent to the first end of the syringe barrel and a cap assembly engaged with the luer lock. The cap assembly may include a cap body and a seal. The plunger rod may be substantially parallel to a longitudinal axis extending in a longitudinal direction through the chamber of the syringe barrel when the plunger rod is in the pre-use position, and the plunger rod may be substantially aligned along the longitudinal axis of the syringe barrel when the plunger rod is in the use position. The second end of the plunger rod may engage and receive a portion of the syringe barrel when the plunger rod is in the pre-use position.

The plunger rod may include an elongate body with the first end of the plunger rod including one of a receiver and an engagement pivotally secured to the other of the receiver and the engagement positioned on the plunger adapter. The plunger adapter may include a stopper engaging portion secured to the stopper body and a plunger interface portion secured to the first end of the plunger rod, with the first end of the plunger rod including one of a receiver and an engagement pivotally secured to the other of the receiver and the engagement positioned on the plunger interface portion of the plunger adapter. The plunger rod may include an extension extending from the elongate body of the plunger rod, with a receiver positioned on the extension of the first end of the plunger rod and an engagement positioned on the plunger adapter. The receiver may include an opening defined by the extension of the first end of the plunger rod, with the engagement comprising a pin-shaped member configured to be received by the receiver of the plunger rod. A medication or drug may be disposed within the syringe barrel. The thumb press may be substantially semi-circular.

In a further embodiment, a syringe assembly includes a syringe barrel having a first end, a second end, and a sidewall extending between the first end and the second end, with the sidewall defining a chamber with a longitudinal axis extending therealong. The syringe assembly further includes a stopper disposed at least partially within the chamber, a plunger adapter engaged with the stopper and defining a recessed portion therein, and a plunger rod having a first end pivotally secured to the plunger adapter. The plunger rod is transitionable from a pre-use position in which a portion of the first end is secured to the plunger adapter and the plunger rod extends adjacent the syringe barrel, to a use position in which the first end is entirely received within the recessed portion and the plunger rod is spaced apart from the syringe barrel. The recessed portion and the first end of the plunger rod have corresponding cross-sectional geometries configured to resist pivoting of the plunger rod beyond the longitudinal axis of the syringe barrel.

The cross-sectional geometry of the first end of the plunger rod may be T-shaped, and the cross-sectional geometry of the recessed portion may be T-shaped and dimensioned to accommodate the first end of the plunger rod therein. The cross-sectional geometry of the first end of the plunger rod may be cross-shaped, and the cross-sectional geometry of the recessed portion may be cross-shaped and dimensioned to accommodate the first end of the plunger rod therein. The stopper and the plunger adapter may be co-formed.

Further details and advantages of the invention will become clear upon reading the following detailed description in conjunction with the accompanying drawing figures, wherein like parts are designated with like reference numerals throughout.

DESCRIPTION OF PREFERRED EMBODIMENTS

For purposes of the description hereinafter, spatial orientation terms, if used, shall relate to the referenced embodiment as it is oriented in the accompanying drawing figures or otherwise described in the following detailed description. However, it is to be understood that the embodiments described hereinafter may assume many alternative variations and embodiments. It is also to be understood that the specific devices illustrated in the accompanying drawing figures and described herein are simply exemplary and should not be considered as limiting.

Referring to FIGS. 1-10, a syringe assembly, generally indicated as 10, adapted for the dispensing and delivery of a fluid is shown. Syringe assembly 10 is intended for use for injection or infusion of fluid, such as a medication, directly into a patient, and is generally shown and described for purposes of the present description as a hypodermic syringe. Syringe assembly 10 is contemplated for use in connection with a needle such as by connecting syringe assembly 10 to a separate needle assembly (not shown), or alternatively for connection with a separate intravenous (IV) connection assembly (not shown).

Figure 1:
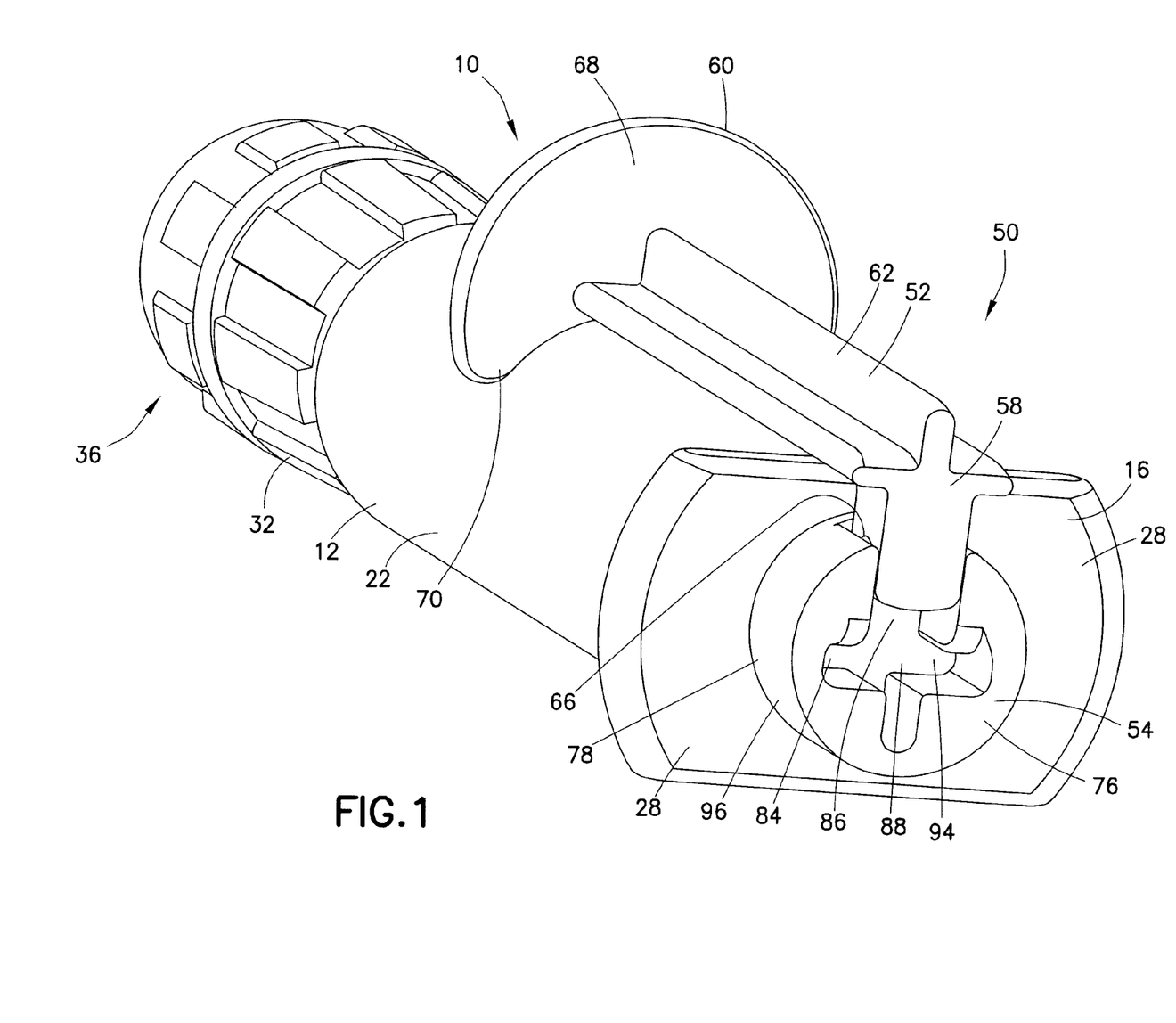
FIG. 1 is a perspective view of a syringe assembly in a pre-use position in accordance with an embodiment of the present invention.
Figures 2, 3, 4:
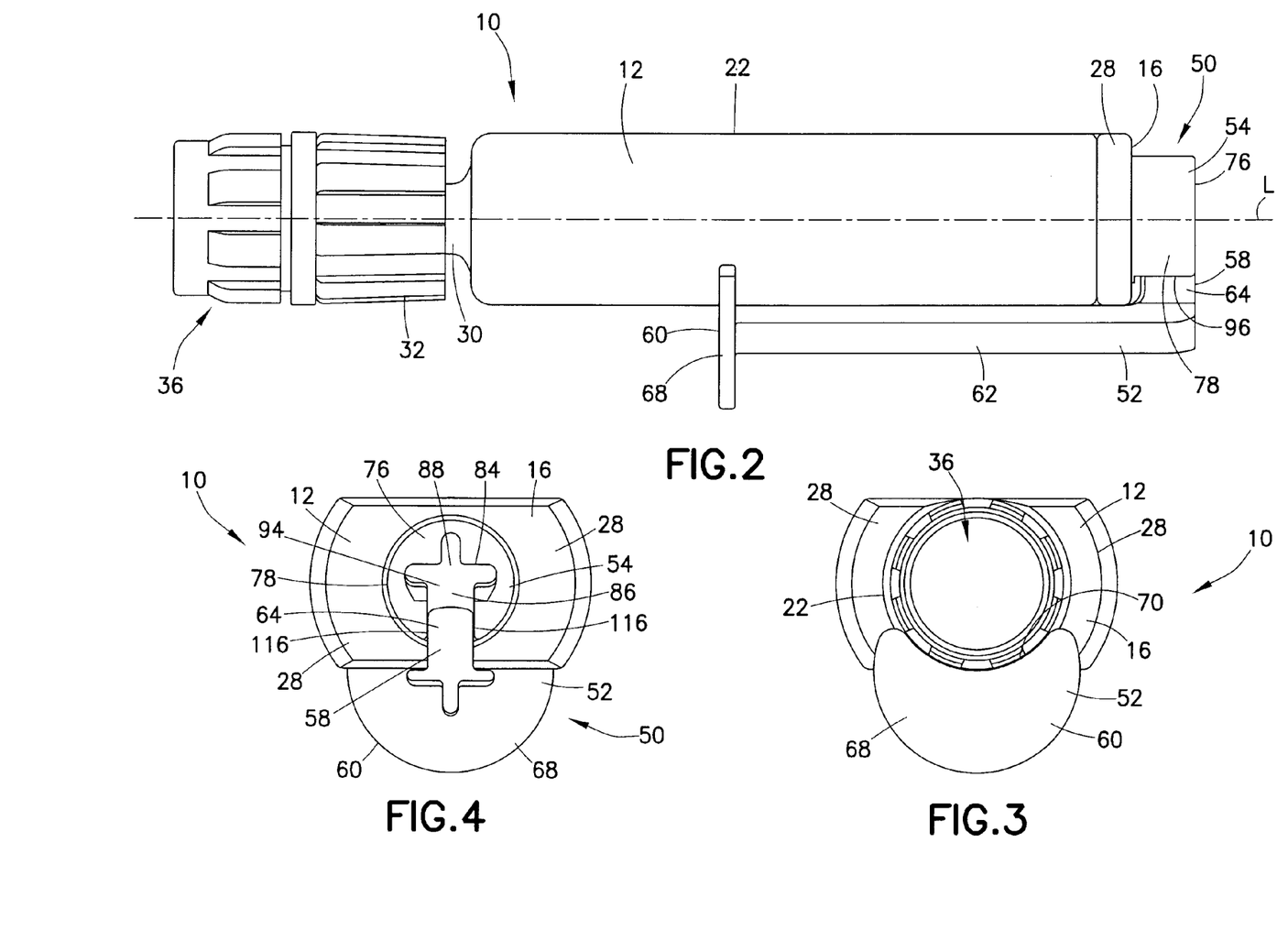
FIG. 2 is a front view of the syringe assembly of FIG. 1 in accordance with an embodiment of the present invention.
FIG. 3 is a right side view of the syringe assembly of FIG. 1 in accordance with an embodiment of the present invention.
FIG. 4 is a left side view of the syringe assembly of FIG. 1 in accordance with an embodiment of the present invention.
Figure 5:
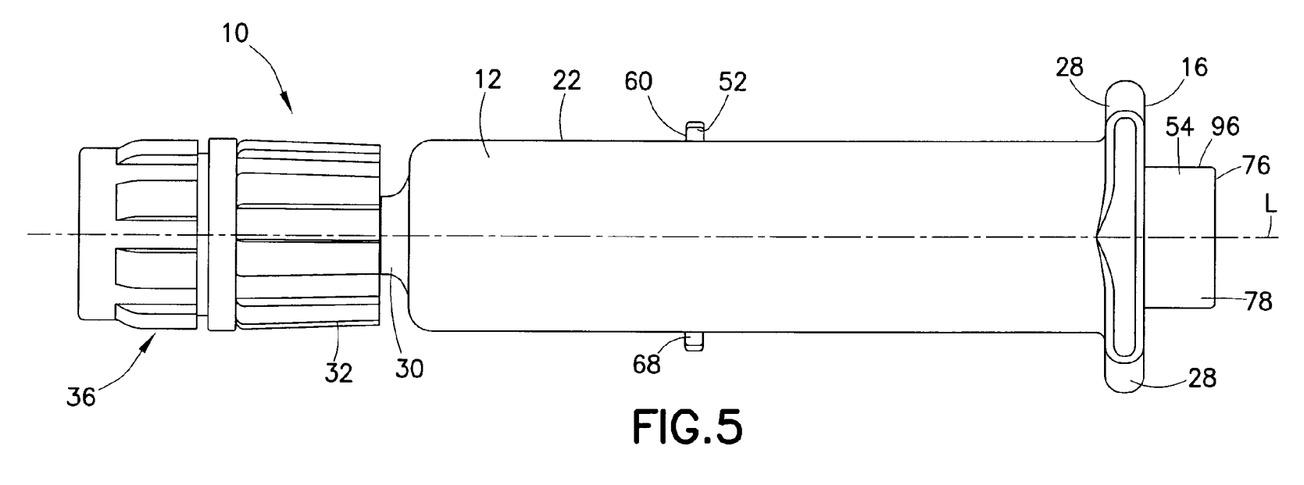
FIG. 5 is a top view of the syringe assembly of FIG. 1 in accordance with an embodiment of the present invention.
Figure 6:
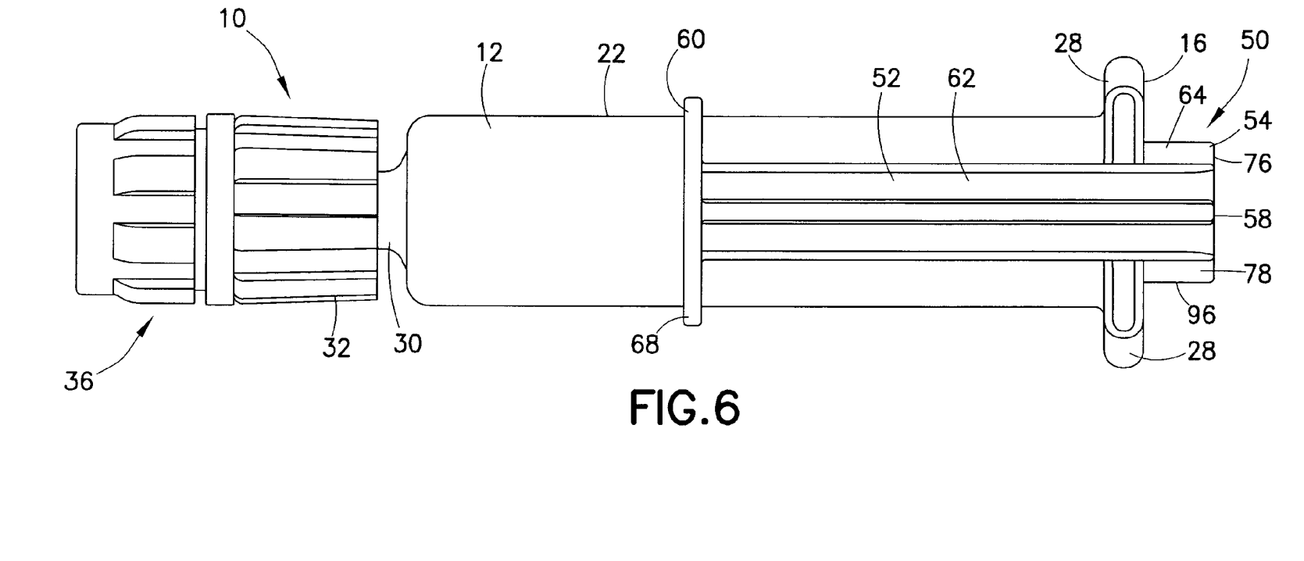
FIG. 6 is a bottom view of the syringe assembly of FIG. 1 in accordance with an embodiment of the present invention.

The syringe assembly 10 includes a syringe barrel 12 having a first or distal end 14 and a second or proximal end 16, with a sidewall 18 extending therebetween and defining an interior chamber 20 of the syringe barrel 12. The syringe barrel 12 defines a longitudinal axis L, as shown in FIG. 2, extending in a longitudinal direction through the interior chamber 20 of the syringe barrel 12. The syringe barrel 12 has an external surface 22 and may be in the general form of an elongated cylindrical barrel, as is known in the art for the general shape of a hypodermic syringe, although other forms for containing a fluid for delivery are also contemplated by the present invention. The first end 14 of the syringe barrel 12 defines an outlet opening 24, and the second end 16 of the syringe barrel 12 defines a rearward opening 26. The syringe barrel 12 may be formed of glass, or may be injection molded from thermoplastic material such as polypropylene and polyethylene according to techniques known to those of ordinary skill in the art, though it is to be appreciated that the syringe barrel 12 may be made from other suitable materials and according to other applicable techniques. In certain configurations, the syringe barrel 12 may include outwardly extending flanges 28 about at least a portion of the second end 16. The flanges 28 may be configured for easy grasping by a medical practitioner, as will be discussed herein.

The syringe barrel 12 may include markings, such as graduations on the sidewall 18 thereof, for providing an indication as to the level or amount of fluid contained within the syringe barrel 12. Such markings may be provided on the external surface 22, the internal wall, or integrally formed or otherwise within the wall of syringe barrel. Alternatively, or in addition thereto, the markings may provide a description of the contents of the syringe, or other identifying information, as may be known in the art.

Figure 7:
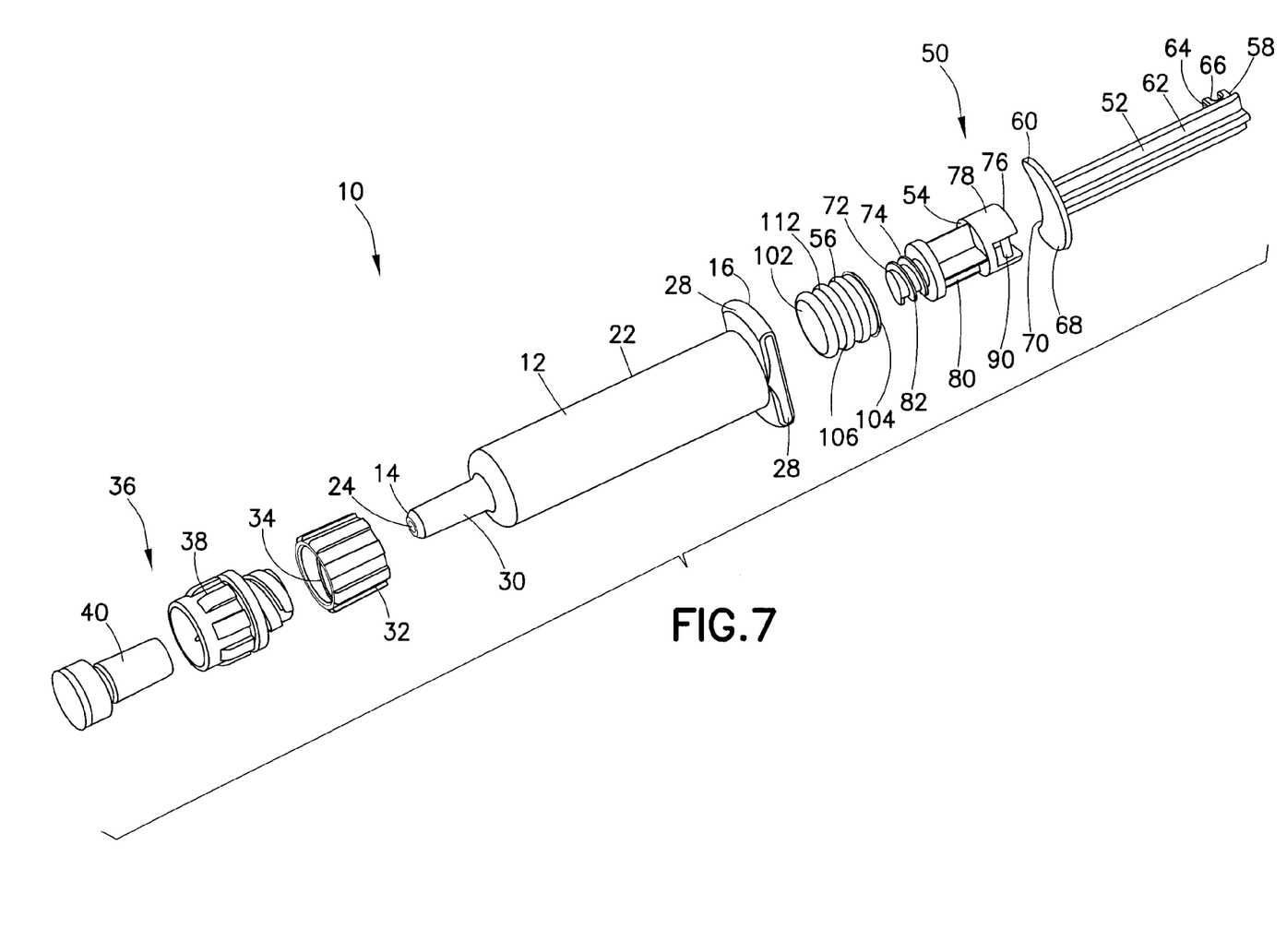
FIG. 7 is an exploded perspective view of the syringe assembly of FIG. 1 in accordance with an embodiment of the present invention.
Figure 8:
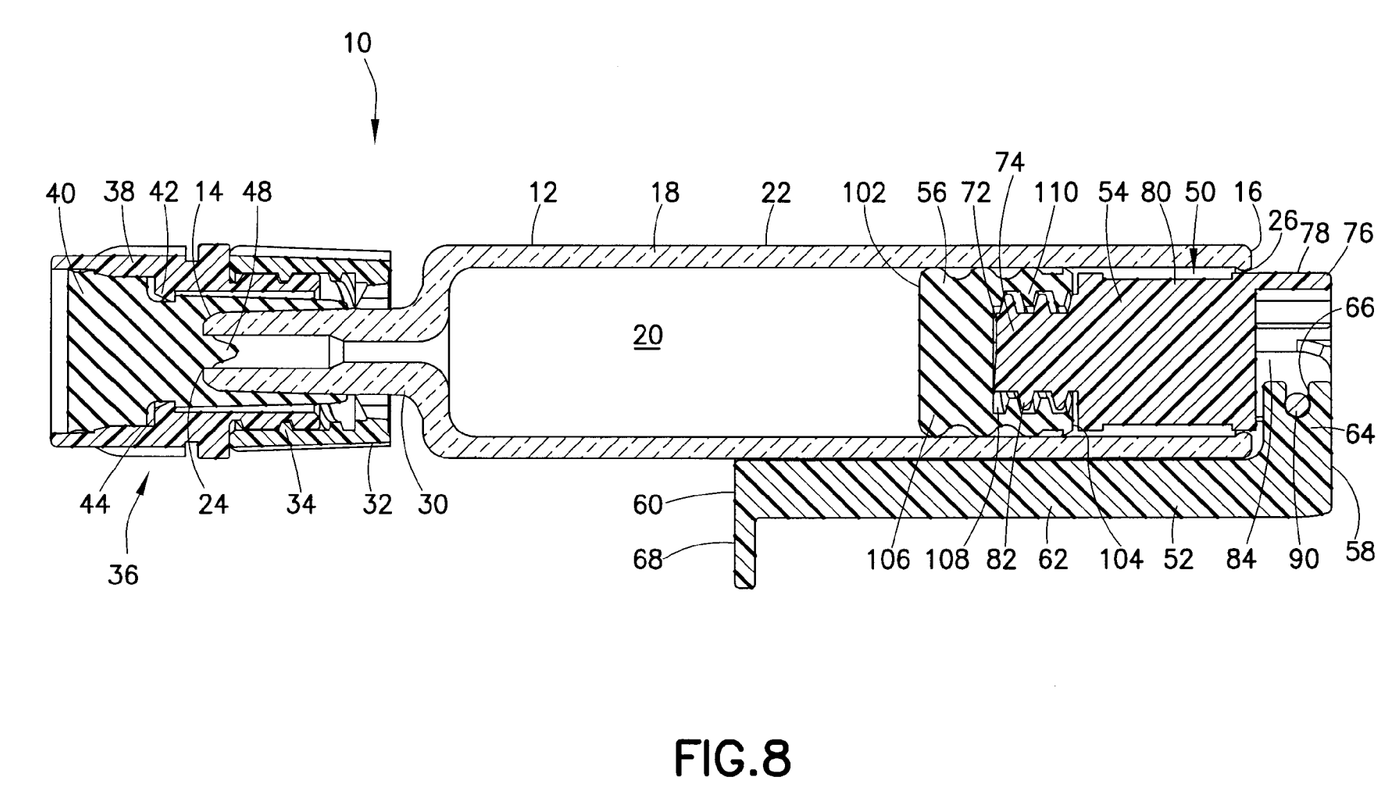
FIG. 8 is cross-sectional view of the syringe assembly of FIG. 1 in accordance with an embodiment of the present invention.
Figure 11:
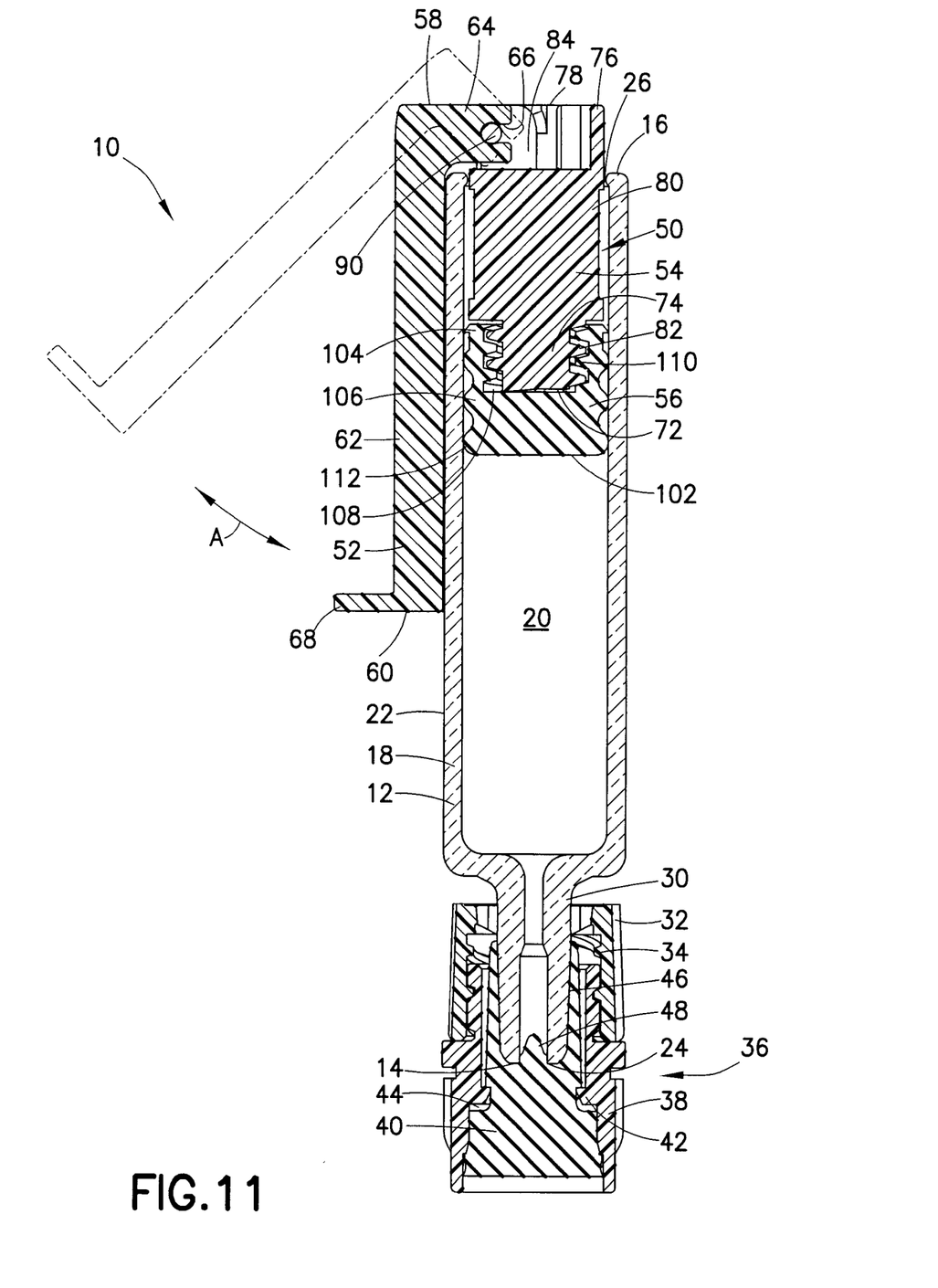
FIG. 11 is a cross-sectional view of the syringe assembly of FIG. 1 showing the plunger rod pivoting away from the syringe barrel in accordance with an embodiment of the present invention.

The first end 14 of syringe barrel including the outlet opening 24 may have a profile adapted for engagement with a separate dispensing device, such as a needle assembly or IV connection assembly, and therefore may include a mechanism for such engagement, for example, a generally tapered luer tip 30, for engagement with a separate luer lock 32. In one configuration, both the tapered luer tip 30 and the separate luer lock 32 may be provided with the syringe assembly. In this configuration, the luer lock 32 may be provided with an attachment mechanism, such as a threaded engagement 34, for corresponding engagement with a cap assembly 36 having a cap body 38 and a seal 40. The seal 40 is secured within the cap body 38 and is configured to close and seal the outlet opening 24 of the first end 14 of the syringe barrel 12 when the cap assembly 36 is engaged with the luer lock 32. The seal 40 is secured within the cap body 38 via an inwardly extending protrusion 42 of the cap body 38 engaging a corresponding recessed portion 44 of the seal 40. The seal 40 defines an opening 46 that receives the luer tip 30 and includes a projection 48 positioned within the opening 46 that is configured to seal the outlet opening 24, as shown in FIG. 11. In another configuration, the tapered luer tip 30 may be provided for direct engagement with a separate device (not shown). In addition, a mechanism for locking engagement therebetween may also be provided. Such luer connections and luer locking mechanisms are well known in the art.

The syringe assembly 10 further includes a plunger assembly 50, at least a portion of which is adapted to be disposed at least partially within the syringe barrel. The plunger assembly 50 provides a mechanism for dispensing fluid contained within the interior chamber 20 of the syringe barrel 12. In particular, the plunger assembly 50 includes a plunger rod 52, a plunger adapter 54, and a stopper 56.

Referring again to FIGS. 1-10, the stopper 56 is positioned within the interior chamber 20 of the syringe barrel 12 at a position adjacent to the rearward opening 26 of the syringe barrel 12. The plunger adapter 54 may be secured to the stopper 56 via an engagement of a stopper engaging portion 74 with a threaded portion 110 in an opening 108 of the stopper 56. In one embodiment, the plunger adapter 54 is formed separately from the stopper 56. In another embodiment, the plunger adapter 54 may be formed integrally with the stopper 56.

The stopper 56 has a first end 102 and a second end 104 and includes an elongate body 106 that is generally cylindrical. In one embodiment, the elongate body 106 of the stopper 56 may define an opening 108 configured to receive the stopper engaging portion 74 of the plunger adapter 54, as will be discussed herein. The stopper 56 may include a threaded portion 110 positioned within the opening 108 that is configured to receive and engage a threaded portion 82 of the stopper engaging portion 74 of the plunger adapter 54. The elongate body 106 of the stopper 56 also includes one or more annular ribs 112 extending about the outside of the stopper 56 for providing sealing engagement with the interior surface of the sidewall 18 of the syringe barrel 12.

The plunger rod 52 has a first end 58 and a second end 60 and includes an elongate body 62 that may be generally T-shaped in cross-section. The first end 58 of the plunger rod 52 includes an extension 64 extending from the elongate body 62 of the plunger rod 52. The extension 64 is generally rectangular and extends from the elongate body 62 substantially perpendicular to, such as at about a 90 degree angle, the elongate body 62 of the plunger rod 52. The extension 64 of the plunger rod 52 includes a receiver 66 that is configured to receive an engagement positioned on the plunger adapter 54. The receiver 66 is a slot-shaped opening defined by the extension 64 of the plunger rod 52, although other suitable arrangements for receiving an engagement may be utilized. The second end 60 of the plunger rod 52 includes a thumb press 68 extending from the elongate body 62 of the plunger rod 52 and defining a recessed portion 70 that is configured to receive and engage the external surface 22 of the sidewall 18 of the syringe barrel 12. The recessed portion 70 of the thumb press 68 is generally semi-spherical shaped and may have a radius that is about the same as a radius of the external surface 22 of the sidewall 18 of the syringe barrel 12.

The plunger adapter 54 has a first end 72 with a stopper engaging portion 74, a second end 76 with a plunger interface portion 78, and an intermediate portion 80 positioned between the first and second ends 72, 76. The stopper engaging portion 74 of the plunger adapter 54 includes a threaded portion 82 configured to engage a corresponding threaded portion of the stopper 56. The threaded portion 82 is a helical thread, although other suitable arrangements may be utilized. The plunger interface portion 78 of the plunger adapter 54 defines a recessed portion 84. As shown more clearly in FIGS. 9 and 10, the recessed portion 84 is generally cross-shaped having a first area 86 configured to receive the extension 64 of the plunger rod 52, and a second area 88 configured to receive the T-shaped cross-section of the elongate body 62 of the plunger rod 52. The plunger interface portion 78 of the plunger adapter 54 also includes an engagement 90 positioned within the second area 88 of the recessed portion 84. The engagement 90 is configured to be received by the receiver 66 of the plunger rod 52 and to allow pivotal movement of the plunger rod 52 relative to the plunger adapter 54.

Figure 9:
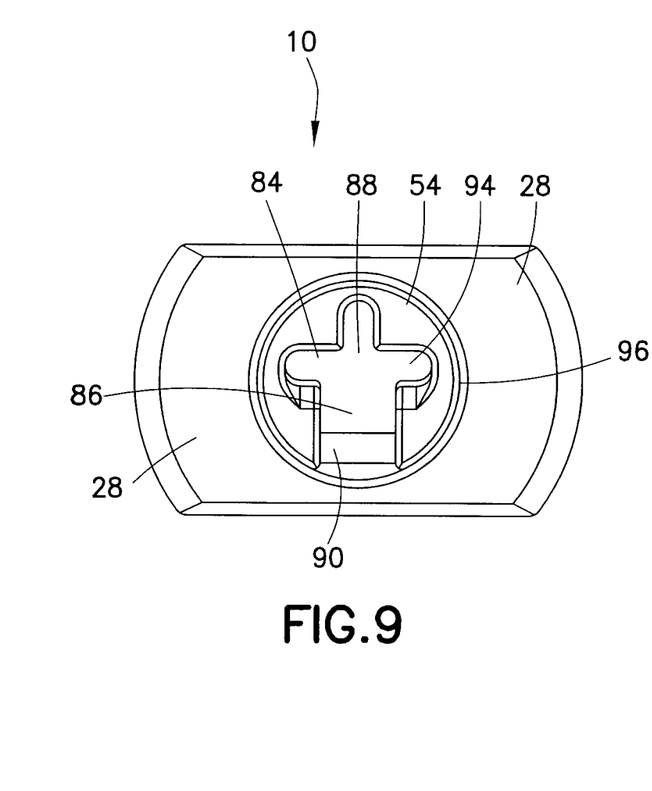
FIG. 9 is an enlarged right side view of the syringe assembly of FIG. 1 with the plunger rod removed in accordance with an embodiment of the present invention.
Figure 10:
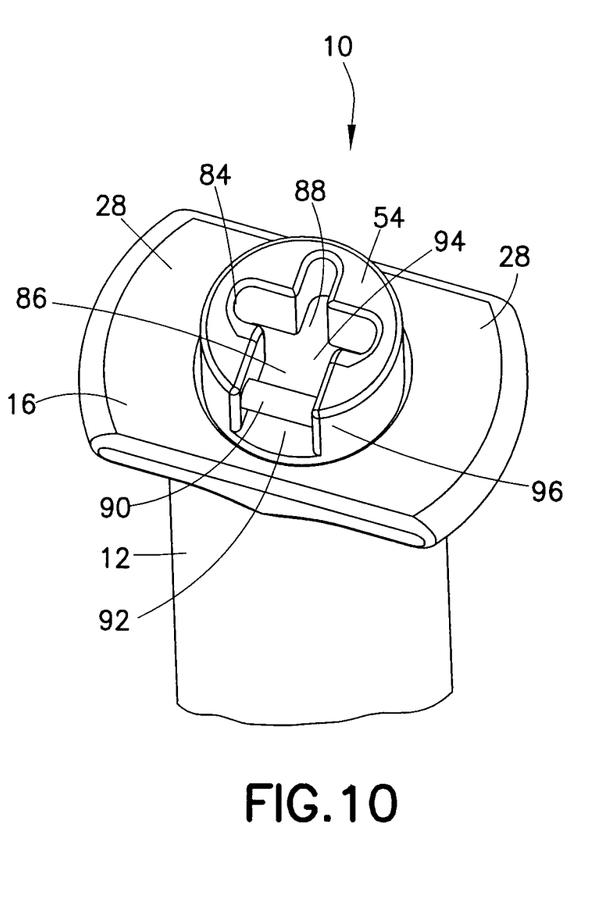
FIG. 10 is a partial perspective view of the syringe assembly of FIG. 1 with the plunger rod removed in accordance with an embodiment of the present invention.

The engagement 90 of the plunger adapter 54 may include a pin-shaped member generally having a cylindrical shape, although other suitable arrangements for the engagement may be utilized. The engagement 90 of the plunger adapter 54 defines a space 92 between the engagement 90 and a bottom surface 94 of the recessed portion 84 of the plunger adapter 54. The engagement 90 of the plunger adapter 54 is spaced radially inward from an external surface 96 of the plunger adapter 54 and is positioned between the first and second ends 72, 76 of the plunger adapter 54. The intermediate portion 80 of the plunger adapter 54 is generally cross-shaped in cross-section, although other suitably shaped portions may be provided between the plunger interface portion and the stopper engaging portion.

The first end 58 of the plunger rod 52 is pivotally secured to the plunger adapter 54 via the connection of the receiver 66 of the plunger rod 52 with the engagement 90 of the plunger adapter 54. In particular, the engagement 90 of the plunger adapter 54 has a friction fit with the receiver 66 of the plunger rod 52 to secure the plunger rod 52 to the plunger adapter 54 and stopper 56 while still allowing pivotal movement of the plunger rod 52 relative to the plunger adapter 54. Although a friction fit arrangement is disclosed, other suitable arrangements for pivotally securing the plunger rod 52 to the plunger adapter 54 may be utilized.

As discussed in more detail below, the plunger rod 52 has a pre-use position (shown in FIG. 11) and a use position (shown in FIG. 12). In the pre-use position, the second end 60 of the plunger rod 52 is positioned adjacent to the syringe barrel 12. In one embodiment, the recessed portion 70 of the thumb press 68 has a profile which substantially corresponds to the exterior surface 22 of the syringe barrel 12. In another embodiment, the recessed portion 70 of the thumb press 68 receives and engages the exterior surface 22 of the syringe barrel 12. The plunger rod 52 is substantially parallel to the longitudinal axis L of the syringe barrel 12, and the plunger interface portion 78 of the plunger adapter 54 is positioned outside of the chamber 20 of the syringe barrel 12 when the plunger rod 52 is in the pre-use position. In the use position, the second end 60 of the plunger rod 52 is spaced from the syringe barrel 12 and the plunger rod 52 is configured to displace the stopper 56 relative to the syringe barrel 12. The plunger rod 52 is substantially aligned with the longitudinal axis L of the syringe barrel 12 when in the use position. When the plunger rod 52 is in the pre-use position and the use-position, the recessed portion 84 of the plunger adapter 54 receives a portion of the first end 58 of the plunger rod 52. In particular, the first area 86 of the recessed portion 84 of the plunger adapter 54 receives the extension 64 of the plunger rod 52 when the plunger rod 52 is in the pre-use position and the use-position. In the use position, the recessed portion 84 of the plunger adapter 54 further receives a portion of the elongate body 62 of the plunger rod 52.

The syringe assembly 10 is particularly useful as a pre-filled syringe, and therefore may be provided for end use with a fluid, such as a medication, contained within interior chamber 20 of syringe barrel 12, pre-filled by the manufacturer. In this manner, the syringe assembly 10 can be manufactured, pre-filled with a medication, sterilized, and optionally packaged in separate packaging, for delivery, storage, and use by the end user, without the need for the end user to fill the syringe with medication from a separate vial prior to use.

Figure 12:
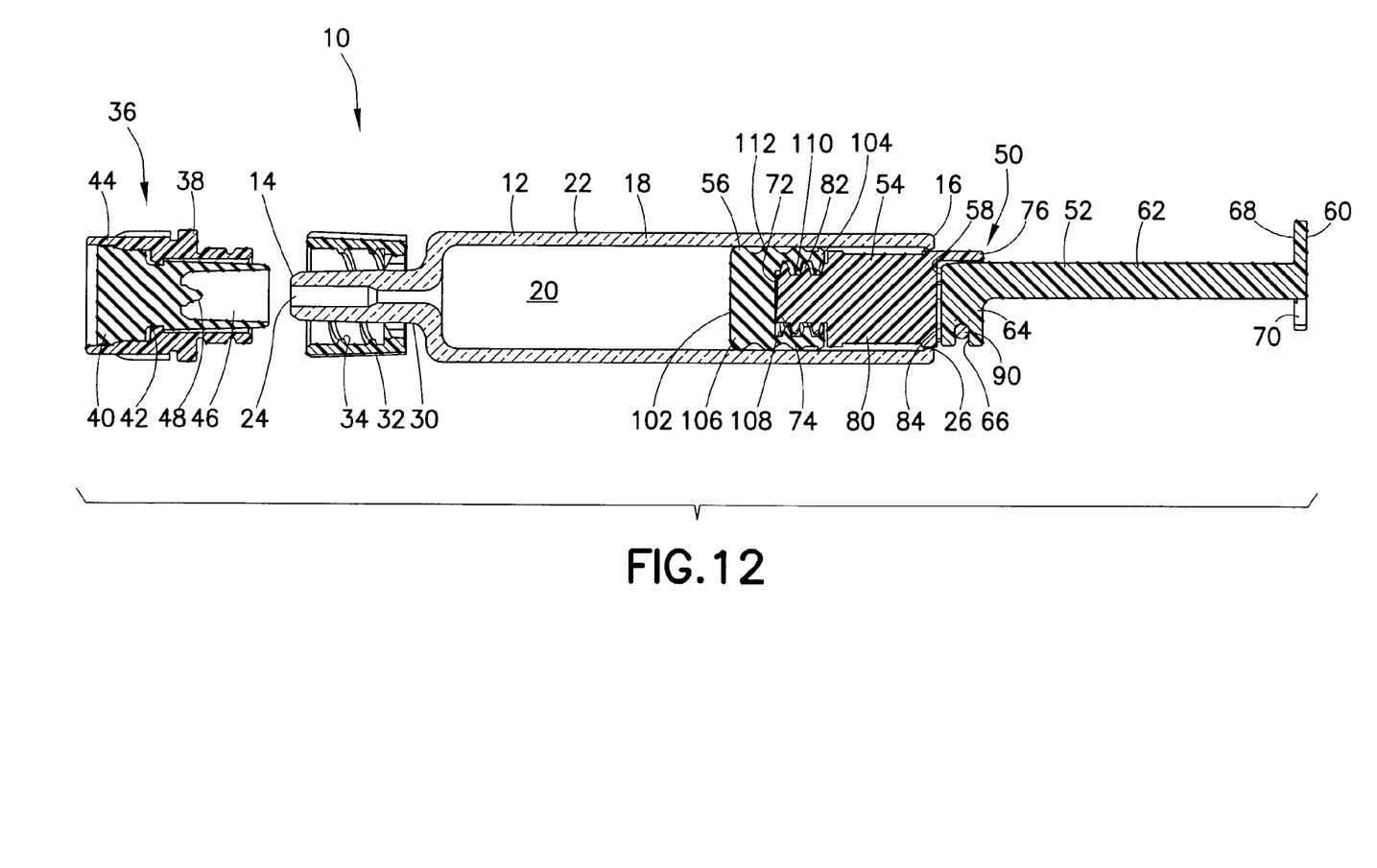
FIG. 12 is a cross-sectional view of the syringe assembly of FIG. 1 showing the plunger rod in a use position in accordance with an embodiment of the present invention.

Referring to FIGS. 11-14B, in use, a user manually pivots the plunger rod 52 from the pre-use position (shown in FIG. 11) to the use position (shown in FIG. 12). As shown in FIG. 11, the second end 60 of the plunger rod 52 is pivoted away from the syringe barrel 12 in a first direction A. The position of the plunger rod 52 between the pre-use position and the use position is shown in phantom lines in FIG. 11. As shown in FIG. 12, the cap assembly 36 is removed from the first end 14 of the syringe barrel and the second end 60 of the plunger rod 52 is further pivoted in the first direction A (shown in FIG. 11) until the plunger rod 52 is in the use position with continued pivoting of the plunger rod 52 being restricted by engagement of the first end 58 of the plunger rod 52 with the plunger adapter 54. In particular, as shown more clearly in FIGS. 12, 14A, and 14B, the recessed portion 84 of the plunger adapter 54 receives the extension 64 of the plunger rod 52 and a portion of the elongate body 62 of the plunger rod 52, thereby preventing continued pivoting in the first direction A. In other words, the recessed portion 84 of the plunger adapter 54 receives the first end 58 of the plunger rod 52 and acts as a stop to prevent further pivoting of the plunger rod 52 in the first direction A when the plunger rod reaches the use position.

Figure 14A:
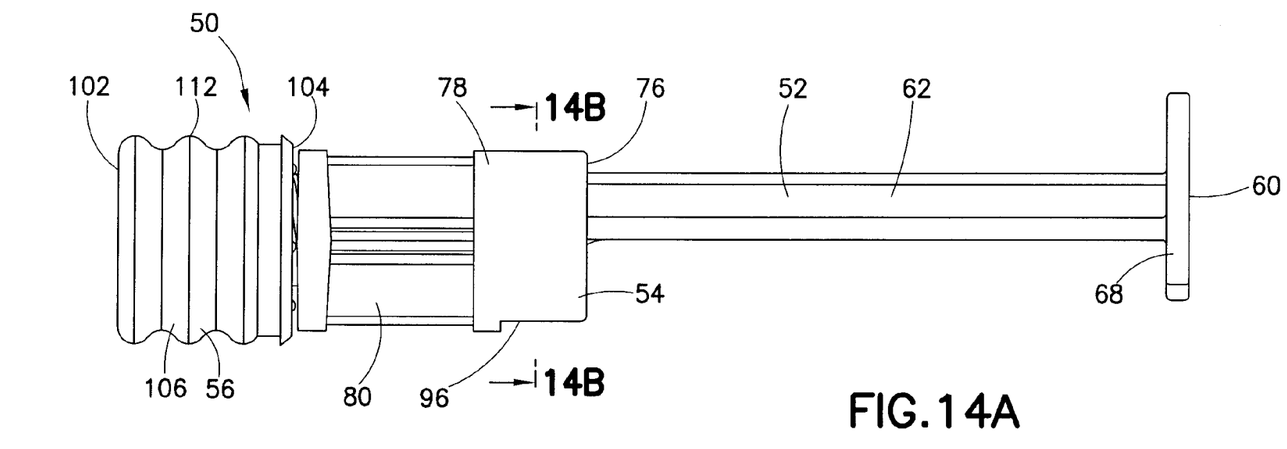
FIG. 14A is a front view of a plunger assembly from the syringe assembly of FIG. 1 in accordance with an embodiment of the present invention.
Figure 14B:
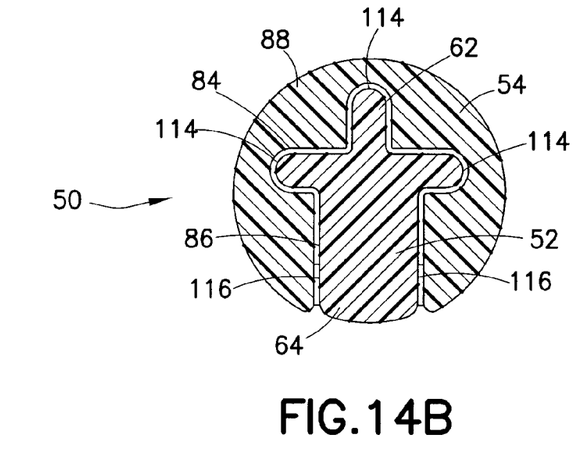
FIG. 14B is a cross-sectional view taken along line 14B-14B of FIG. 14A showing the plunger rod in a use position in accordance with an embodiment of the present invention.

Furthermore, the plunger rod 52 is stabilized in the use position through the positioning of the first end 58 of the plunger rod 52 within the recessed portion 84. More specifically, the T-shaped cross-section of the elongate body 62 of the plunger rod 52 and the correspondingly shaped second area 88 of the recessed portion 84 of the plunger adapter 54 cooperate to provide multiple surfaces of engagement 114 between the plunger rod 52 and the plunger adapter 54 thereby stabilizing the connection therebetween. The engagement surfaces 114 may also be positioned substantially perpendicular, such as at 90 degree angles, relative to each other to stabilize the plunger rod 52 when torque is applied to the plunger rod 52 during deployment thereof into the syringe barrel 12. Also, pivoting of the plunger rod 52 from the pre-use position to the use position is stabilized due to the positioning of the extension 64 of the plunger rod 52 within the first area 86 of the recessed portion 84 of the plunger adapter 54 during movement from the pre-use position to the use position. In particular, positioning the extension 64 of the plunger rod 52 within the first area 86 of the recessed portion 84 in the pre-use position provides engagement surfaces 116 on each side of the extension 64 to stabilize the pivoting movement of the plunger rod 52.

Figure 13:
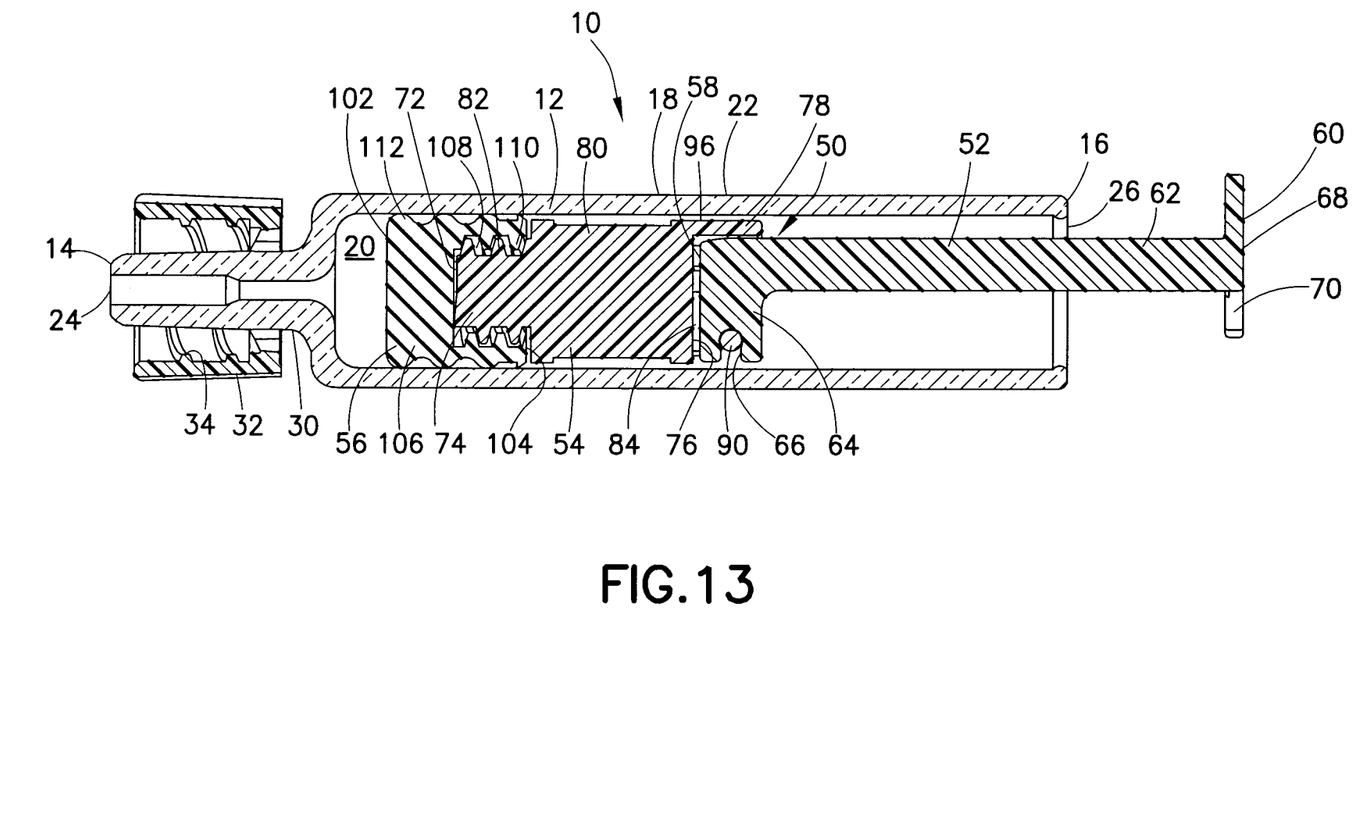
FIG. 13 is a cross-sectional view of the syringe assembly of FIG. 1 showing the plunger rod in a depressed position in accordance with an embodiment of the present invention.

When the plunger rod 52 is in the use position, the syringe assembly 10 can be grasped with the user's thumb on the thumb press 68 of the plunger rod 52 and with the user's fingers grasping the flanges 28. In this manner, the syringe assembly 10 is grasped by the user in a well known and well recognized manner. As shown in FIG. 13, the user effects a squeezing movement between the thumb and forefingers thereby depressing plunger rod 52 into the rearward opening 26 of the syringe barrel 12. Such movement transfers to the plunger adapter 54 and stopper 56 causing movement of the stopper 56 and plunger adapter 54 within the interior chamber 20 of the syringe barrel 12, reducing the volume of the interior chamber 20, and creating a positive pressure therein.

Prior to the dispensing of medication, any air trapped within interior chamber 20 may be expelled by initial movement of plunger rod 52 into syringe barrel 12 in a known manner. The user can attach luer tip 30 to a separate needle assembly or IV connection assembly and lockingly engage through threads of the luer lock 32 in a known manner. The medication fluid within interior chamber 20 is forced out through outlet opening 24 at first end 14 of syringe barrel 12. In this manner, the fluid medication can be expelled from the syringe barrel 12 through outlet opening 24 and into the separate needle assembly or IV assembly and into the patient.

Upon full movement of the stopper 56 through syringe barrel 12, the stopper "bottoms out". The stopper 56, as shown in FIG. 13, is not fully depressed and is just short of bottoming out. After bottoming out and dispensing all of the fluid within the interior chamber 20 of the syringe barrel 12, the syringe assembly 10 can be detached from the patient and appropriately discarded. Although the use of the syringe assembly 10 was described in connection with a pre-filled syringe, the syringe assembly 10 may also be utilized for aspiration by moving the stopper 56 to the position shown in FIG. 13 and retracting the stopper 56 by moving the second end 60 of the plunger rod 52 away from the syringe barrel 12.

The syringe assembly 10 may be positioned within a separate container or package prior to use. In particular, the syringe assembly 10 may be packaged within a blister pack, as is known in the art, although other suitable package arrangements may be utilized. Further, in storage, the syringe assembly 10 may be placed in a controlled environment in which space is limited. The profile of the syringe assembly 10 of the present invention, however, is significantly reduced from conventional pre-filled syringes having the plunger extending from the barrel prior to use. In particular, pivotally securing the plunger rod 52 to the plunger adapter 54 and stopper 56 reduces the length of the syringe assembly 10 from conventional pre-filled syringes. Also, as discussed above, the second end 60 of the plunger rod 52 of the syringe assembly 10 is configured to conform to the external surface 22 of the sidewall 18 of the syringe barrel 12 further reducing the profile or footprint of the syringe assembly 10 thereby conserving space in storage.

Figure 15:
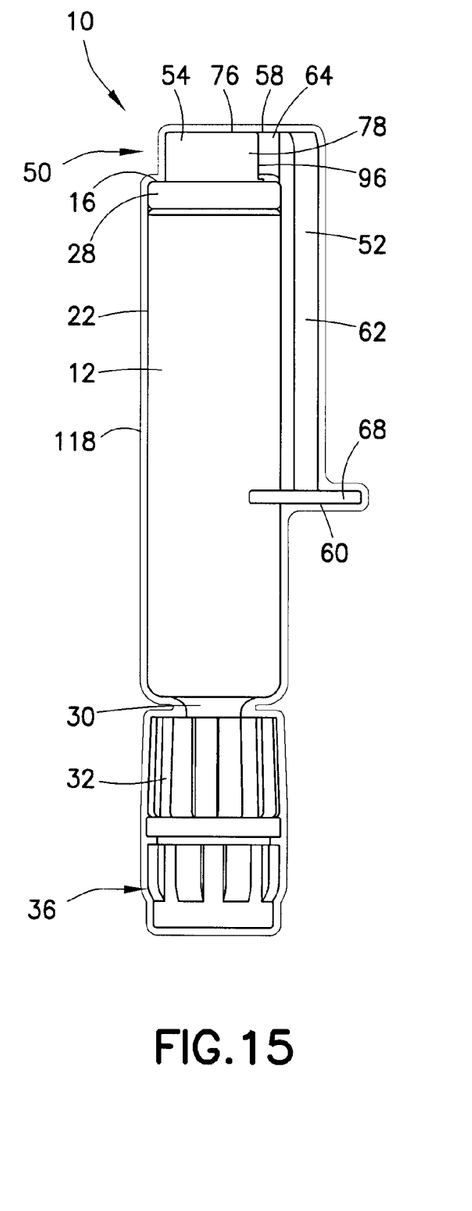
FIG. 15 is a front view of the syringe assembly of FIG. 1 in accordance with an embodiment of the present invention, showing a layer of shrink wrap covering the syringe assembly.
Figure 16:
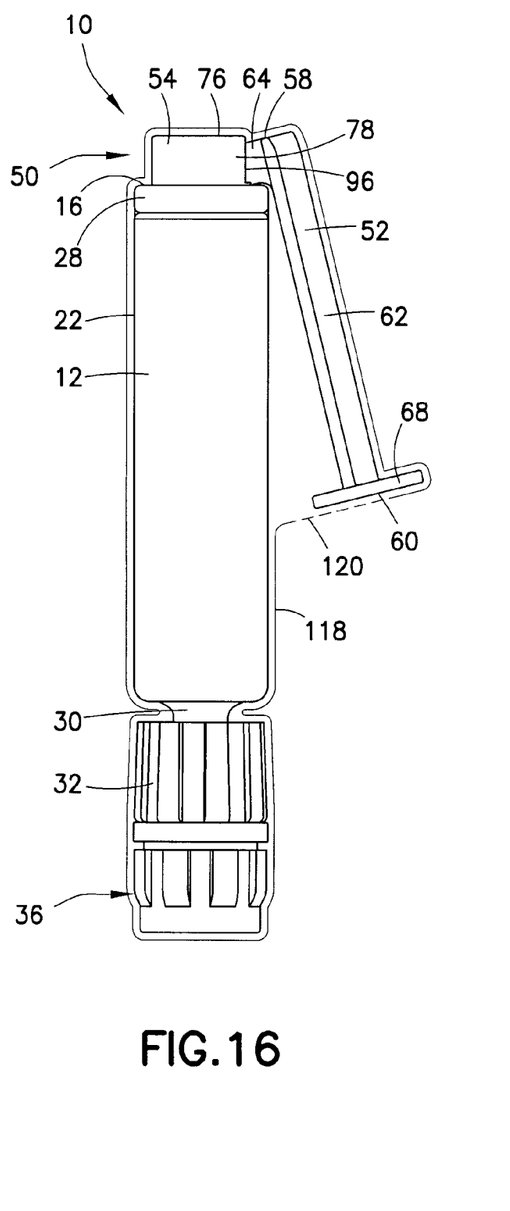
FIG. 16 is a front view of the syringe assembly of FIG. 1 in accordance with an embodiment of the present invention, showing a layer of shrink wrap being torn by a pivoting plunger rod.

Referring to FIGS. 15 and 16, in one embodiment, the syringe assembly 10 is covered by a layer of shrink wrap 118 that extends around the perimeter of the syringe assembly 10. The layer of shrink wrap 118 encapsulates the syringe assembly 10 to maintain the sterility of the syringe assembly 10. As shown in FIG. 16, pivoting the plunger rod 52 from the pre-use position and away from the syringe barrel 12, as described above, tears the layer of shrink wrap 118 to form an opening 120 and allows removal of the syringe assembly 10 from the shrink wrap 118. The layer of shrink wrap 118 may include a weakened portion adjacent to the second end 60 of the plunger rod 52 to assist in tearing the shrink wrap 118 at that location upon pivoting of the plunger rod 52.

While several embodiments of a syringe assembly were described in the foregoing detailed description, those skilled in the art may make modifications and alterations to these embodiments without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are embraced within their scope.

What is claimed is:

1. A syringe assembly comprising:
    a syringe barrel having a first end, a second end, and a sidewall extending between the first end and the second end, the sidewall defining a chamber;
    a stopper disposed within the chamber of the syringe barrel;
    a plunger adapter engaged with the stopper, the plunger adapter defining a recessed portion therein, wherein the recessed portion defines a first area and a second area, the second area being cross-shaped; and
    a plunger rod having first and second ends, the plunger rod comprising an elongate body and an extension extending from the elongate body, the first end of the plunger rod pivotally secured to the plunger adapter, the plunger rod having a pre-use position-wherein the second end of the plunger rod is positioned adjacent to the syringe barrel, and a use position wherein the plunger rod is configured to displace the stopper relative to the syringe barrel, the recessed portion of the plunger adapter receiving a portion of the first end of the plunger rod when the plunger rod is in the pre-use position and the use position,
    wherein, in the use position, the elongate body is received within the second area of the recessed portion and the extension is received within the first area of the recessed portion.

2. The syringe assembly of claim 1, wherein the stopper and the plunger adapter are co-formed.

3. The syringe assembly of claim 1, wherein the syringe barrel defines a longitudinal axis extending in a longitudinal direction through the chamber, the plunger rod substantially parallel to the longitudinal axis of the syringe barrel when the plunger rod is in the pre-use position and substantially aligned along the longitudinal axis of the syringe barrel when the plunger rod is in the use position.

4. The syringe assembly of claim 3, wherein the second end of the plunger rod engages and receives a portion of the syringe barrel when the plunger rod is in the pre-use position.

5. The syringe assembly of claim 1, wherein the first end of the plunger rod includes one of a receiver or an engagement, wherein the receiver or the engagement is pivotally secured to the other of the receiver or the engagement, wherein the other of the receiver or the engagement is positioned within the recessed portion of the plunger adapter.

6. The syringe assembly of claim 1, further comprising an engagement positioned within the recessed portion of the plunger adapter for receiving the extension in the use position.

7. The syringe assembly of claim 6, wherein the receiver comprises an opening corresponding to the extension, and wherein the engagement comprises a pin-shaped member configured to be received by the receiver of the plunger rod.

8. The syringe assembly of claim 7, wherein at least a portion of the plunger rod is generally T-shaped in cross-section, and wherein the recessed portion of the plunger adapter is configured to receive the plunger rod therein in the use position.

9. The syringe assembly of claim 8, wherein the recessed portion of the plunger adapter is generally cross-shaped having a first area configured to receive the extension and a second area configured to receive the T-shaped cross-section of the plunger rod.

10. The syringe assembly of claim 1, wherein the first end of the plunger rod is pivotally secured to the plunger adapter at a position spaced radially inward from an external surface of the plunger adapter.

11. A syringe assembly comprising:
    a syringe barrel having a first end, a second end, and a sidewall extending between the first end and the second end, the sidewall defining a chamber;
    a stopper;
    a plunger adapter engaged with the stopper, at least a portion of the stopper positioned within the chamber of the syringe barrel, wherein the plunger adapter defines a recessed portion wherein the recessed portion defines a first area and a second area; and
    a plunger rod comprising an elongate body and an extension extending from the elongate body, the plunger rod having a first end pivotally secured to the plunger adapter and a second end comprising a thumb press having a recessed portion configured to conform to an external surface of the syringe barrel, the plunger rod having a pre-use position wherein the second end of the plunger rod is positioned adjacent to the syringe barrel, and a use position wherein the second end of the plunger rod is spaced from the syringe barrel along a longitudinal axis of the syringe barrel, wherein the first area of the recessed portion receives the extension when the plunger rod is in both the pre-use and the use positions and wherein the second area of the recessed portion receives the elongate body when the plunger rod is in the use position.

12. The syringe assembly of claim 11, wherein the stopper and the plunger adapter are co-formed.

13. The syringe assembly of claim 11, further comprising a luer lock positioned adjacent to the first end of the syringe barrel.

14. The syringe assembly of claim 13, further comprising a cap assembly engaged with the luer lock, the cap assembly comprising a cap body and a seal.

15. The syringe assembly of claim 11, wherein the longitudinal axis extends in a longitudinal direction through the chamber, the plunger rod substantially parallel to the longitudinal axis of the syringe barrel when the plunger rod is in the pre-use position and substantially aligned along the longitudinal axis of the syringe barrel when the plunger rod is in the use position.

16. The syringe assembly of claim 15, wherein the second end of the plunger rod engages and receives a portion of the syringe barrel when the plunger rod is in the pre-use position.

17. The syringe assembly of claim 11, wherein the second end of the plunger rod engages and receives a portion of the syringe barrel when the plunger rod is in the pre-use position.

18. The syringe assembly of claim 11, wherein the first end of the plunger rod includes one of a receiver or an engagement, wherein the receiver or the engagement is pivotally secured to the other of the receiver or the engagement, wherein the other of the receiver or the engagement is positioned within the recessed portion of the plunger adapter.

19. The syringe assembly of claim 11, wherein the plunger adapter comprises a stopper engaging portion secured to the stopper and a plunger interface portion secured to the first end of the plunger rod, and wherein the first end of the plunger rod includes one of a receiver and an engagement pivotally secured to the other of the receiver and the engagement positioned on the plunger interface portion of the plunger adapter.

20. The syringe assembly of claim 18, wherein the receiver is positioned on an extension of the first end of the plunger rod and the engagement is positioned on the plunger adapter.

21. The syringe assembly of claim 20, wherein the receiver comprises an opening defined by the extension of the first end of the plunger rod, and wherein the engagement comprises a pin-shaped member configured to be received by the receiver of the plunger rod.

22. The syringe assembly of claim 11, further comprising a medication or drug disposed within the syringe barrel.

23. The syringe assembly of claim 11, wherein the thumb press is substantially semi-circular.

24. A syringe assembly comprising:
a syringe barrel having a first end, a second end, and a sidewall extending between the first end and the second end, the sidewall defining a chamber with a longitudinal axis extending therealong;
a stopper disposed at least partially within the chamber;
a plunger adapter engaged with the stopper, the plunger adapter defining a recessed portion therein, the recessed portion defining a first area and a second area; and
a plunger rod having an elongate body having a t-shaped cross-section and an extension extending from the elongate body, a first end pivotally secured to the plunger adapter and transitionable from a pre-use position in which a portion of the first end is secured to the plunger adapter and the plunger rod extends adjacent the syringe barrel, to a use position in which the first end is entirely received within the recessed portion and the plunger rod is spaced apart from the syringe barrel, the first area of the recessed portion receiving the t-shaped elongate body and the second area receiving the extension therein in the use position.

25. The syringe assembly of claim 24, wherein the first area of the recessed portion is T-shaped and dimensioned to accommodate the t-shaped elongate body therein.

26. The syringe assembly of claim 24, wherein the stopper and the plunger adapter are co-formed.

\* \* \* \* \*